United States Patent [19]

Gao et al.

[11] Patent Number: 5,616,808
[45] Date of Patent: Apr. 1, 1997

[54] OPTICALLY PURE 1-AMINO-2-INDANOLS

[75] Inventors: Yun Gao, Framingham; Yaping Hong, Worcester; Xiaoyi Nie, Boxborough; Roger P. Bakale, Shrewsbury; Richard R. Feinberg, Norton; Charles M. Zepp, Berlin, all of Mass.

[73] Assignee: Sepracor, Inc., Marlborough, Mass.

[21] Appl. No.: 321,998

[22] Filed: Oct. 12, 1994

Related U.S. Application Data

[63] Continuation-in-part of Ser. No. 278,459, Jul. 21, 1994, which is a continuation-in-part of Ser. No. 121,340, Sep. 14, 1993, Pat. No. 5,516,943.

[51] Int. Cl.$^6$ .................................................. C07C 211/38
[52] U.S. Cl. .......................................................... 564/428
[58] Field of Search .................................... 564/443, 428

[56] References Cited

U.S. PATENT DOCUMENTS 5,043,341  8/1991  Cohen et al. ............................. 514/288

FOREIGN PATENT DOCUMENTS

| 6815088 | 10/1968 | Belgium . |
| 0272982 | 6/1988 | European Pat. Off. . |
| 321175 | 6/1989 | European Pat. Off. . |
| 1462244 | 7/1965 | France . |

OTHER PUBLICATIONS

Tucker et al. "A Series of Potent HIV–1 Protease Inhibitors Containing a . . . " *J. Med. Chem.* 35, 2525–33 (1992).
Young et al. "HIV–1 Protease Inhibitors Based on Hydroxyethylene . . . " *J. Med. Chem.* 35, 1702–1709 (1992).
Thompson et al. "Synthesis and Antiviral Activity of a Series of HIV–1 . . . " *J. Med. Chem.* 35, 1685–1701 (1992).
Armstrong et al. "Stereocontrolled Addition of Chiral, Non–Racemic Amide . . . " *Tetrahedron Letters* 33, 6599–6602 (1992).
Lutz et al. "Further Studies on the Stability of β–Hydroxyethylamines . . . " *J. Am. Chem. Soc.* 73, 1639–1641 (1951).
Jacobsen et al. "Highly Enantioselective Epoxidation Catalysts Derived from 1,2–Diaminocyclohexane" *J. Am. Chem. Soc.* 113, 7063–64 (1991).
Askin et al. "Highly Diastereoselective Alkylations of Chiral Amide" *J. Org. Chem.* 57, 2771–2773 (1992).
Lyle et al. "Benzocycloalkyl Amines as Novel C–Termini for . . . " *J. Med. Chem.* 34, 1228–1230 (1991).
McCasland et al. "Stereochemistry of Aminocyclanols. Synthesis of . . . " *J. Am. Chem. Soc.* 72, 2190–2195 (1950).
Bannard et al. "Reaction of trans–2–Acylaminocyclanols with Thionyl Chloride" *Can. J. Chem.* 49, 2064–2072 (1970).
McCarthy et al. "Stereospecific Syntheses of the Four Diastereomeric" *J. Org. Chem.* 50, 3095–3103 (1985).
Ghosh et al. "Stereoselective Reduction of α–Hydroxy Oxime Ethers . . . " *Tetrahedron Letters* 32, 711–714 (1991).
Hassner et al. "Addition of Iodine Isocyanate to Olefins . . . " *J. Org. Chem.* 32, 540–549 (1967).
Johnson et al. "Ring Closure of the 2–Benzoylaminocyclohexanols . . . " *J. Am. Chem. Soc.* 72, 2187–2190 (1950).
Winstein et al. "The Role of Neighboring Groups in Replacement Reactions . . . " *J. Am. Chem. Soc.* 72, 4669–4677 (1950).
Pracejus et al. "O,N–Bis(diphenylphosphino) derivatives of chiral trans– and cis–2–aminocyclohexanols: synthesis . . . " *J. Prakt. Chem.* 329, 235–45 (1987).
Kotora et al. "Addition of tetrachloromethane to styrene catalyzed by copper–chiral amine complexes" *Coll. Czech. Chem. Commun.* 56, 2622–8 (1992).
Didier et al. "Chemo–enzymatic Synthesis of 1,2– and 1,3–amino alcohols and their use in the . . " *Tetrahedron* 47, 4941–58 (1991).
Drefahl et al. "Aminoalkohole, I: cis– und trans–DL–1–Amino–2–hydroxy–tetralin und . . . " *Chemische Beriuchte* 91, 266–70 (1958).
Braun et al. "Alkamine und Äther–basen der Tetralin– und Hydrinden–Reihe" *Chemische Berichte* 73, 3052–59 (1030).
CA65:113816 (1966).
Posner et al., JACS, 99(5), pp. 821418 (1977).

*Primary Examiner*—Brian M. Burn
*Attorney, Agent, or Firm*—Heslin & Rothenberg, P.C.

[57] ABSTRACT

A two-step process for the conversion of a trans-1-amino-2-hydroxycycloalkane stereoselectively to a cis-1-amino-2-hydroxycycloalkane is disclosed. The novel step, a one-step hydrolysis with formal inversion, can be used to convert an amide of a trans-1-amino-2-hydroxycycloalkane to a cis-1-amino-2-hydroxycycloalkane. Methods for obtaining the trans-1-amino-2-hydroxycycloalkanes and their amides from alkenes are also disclosed, as are the novel, substantially optically pure 1-amino-2-indanols and 1-amido-2-indanols obtained thereby. A preferred process converts indene to cis-1-amino-2-indanol.

5 Claims, No Drawings

OPTICALLY PURE 1-AMINO-2-INDANOLS

CROSS-REFERENCE TO RELATED APPLICATIONS

This is a continuation-in-part of U.S. application Ser. No. 08/278,459, filed Jul. 21, 1994, now pending which is a continuation-in-part of U.S. application Ser. No. 08/121,340, filed Sep. 4, 1993 now U.S. Pat. No. 5,516,943.

FIELD OF THE INVENTION

The invention relates to a process for preparing cyclic cis-1-amino-2-alkanols from cyclic trans-1-amino-2-alkanols or the amides of trans-1-amino-2-alkanols. The invention also relates to 1-amino-2-indanols and derivatives thereof obtained by the foregoing process which are useful as auxiliary reagents for enantioselective reactions.

BACKGROUND OF THE INVENTION cyclic cis-1-amino-2-alkanols are useful as chiral auxiliaries and as intermediates in the synthesis of pharmaceuticals. For example, optically pure cis-(1S,2R)-1-amino-2-indanol(I)

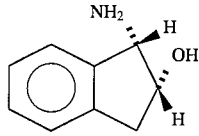

been used as an intermediate in the preparation of HIV-1 protease inhibitors for anti-viral and anti-AIDS therapy (T. J. Tucker et al. *J. Med. Chem.* 35, 2525–2533 (1992); S. D. Young et al. *J. Med. Chem.* 35, 1702–1709 (1992); W. J. Thompson et al. *J. Med. Chem.* 35, 1685–1702 (1992)). In addition, optically pure cis-1-amino-2-indanol has been used as a chiral auxiliary for the asymmetric addition of amide homoenolates to aldehydes (J. D. Armstrong, III, et al. *Tetrahedron Lett.* 44, 6599–6602 (1992)).

Cyclic cis-1-amino-2-alkanols are commonly prepared from the corresponding trans-1-aminoalkanols, which are synthetically much more accessible. For example, Lutz and Wayland have described the preparation of racemic cis-1-amino-2-indanol from racemic trans-1-amino-2-indanol in three steps (R. E. Lutz and R. L. Wayland, Jr., *J. Am. Chem. Soc.* 73, 1639–1641 (1951)). Their synthesis is a particular application of what appears to be the most popular method for converting trans aminoalcohols to cis aminoalcohols. It involves the synthesis of an oxazoline by the treatment of the amide with thionyl chloride. The oxazoline is isolated, usually by crystallization for the purpose of purification, and subsequently hydrolyzed, theoretically via an ester-ammonium salt, to the cis aminoalcohol.

Optically pure cis-(1S,2R)-1-amino-2-indanol has also been obtained by the resolution of the corresponding L-phenylalanine amide diastereomers by chromatographic separation, followed by cleavage of the amide with sodium in ethanol (W. J. Thompson et al. *J. Med. Chem.* 35, 1685–1701 (1992)).

These and other known processes for the preparation of cyclic cis-1-amino-2-alkanols often involve lengthy synthetic transformations and usually provide the desired product in low overall yield. Resolution procedures for obtaining optically pure cis-(1S,2R)-1-amino-2-indanol are notoriously inefficient. A practical preparation of cyclic cis-1-amino-2-alkanols, particularly of optically pure cis-1-amino-2-indanol, would be highly desirable.

It is, therefore, an object of the present invention to provide a process for the preparation of cyclic cis-1-amino-2-alkanols from the corresponding cyclic trans-1-amino-2-alkanols or their amides. It is a particular object of the present invention to prepare cis-1-amino-2-indanol from trans-1-amino-2-indanol in good yield and with a minimum of synthetic manipulations. It is also an object of the present invention to prepare optically pure cis-1-amino-2-alkanols such as cis-(1S,2R)-1-amino-indanol, from the corresponding partially resolved or optically pure trans-1-amino-2-alkanols in good yield and with minimum synthetic transformations.

SUMMARY OF THE INVENTION

The objects of the present invention are provided by a process for the preparation of a racemic or optically pure cyclic cis-1-amino-2-alkanol from the corresponding trans-1-amino-2-alkanol or amide of the trans 1-amino-2-alkanol.

In one aspect the invention relates to a process for the stereospecific conversion of a trans-1-amino-2-hydroxycyclopentane to the corresponding cis-1-amino-2-hydroxycyclopentane comprising:

(a) reacting a trans-1-amino-2-hydroxycyclopentane with an acylating agent to produce an amide; and (b) treating the amide with an aqueous solution of a strong acid to cleave the amide and effect inversion of the carbon bearing the hydroxyl function to produce a cis-1-amino-2-hydroxycyclopentane.

In another aspect the invention relates to a process for the stereospecific conversion of an amide of a trans-1-amino-2-hydroxycyclopentane to the corresponding cis-1-amino-2-hydroxycyclopentane by treating the amide of the trans-1-amino-2-hydroxycyclopentane with a solution of a strong acid to cleave the amide and effect inversion of the carbon bearing the hydroxyl function to produce a cis-1-amino-2-hydroxycyclopentane.

Preferred strong acids include hydrochloric, sulfuric, methanesulfonic and triflic acids. The amide is preferably an acetamide, propanamide, butanamide, benzamide, chlorobenzamide, nitrobenzamide, anisamide or toluamide, most preferably the amide is a benzamide.

In one embodiment the trans-1-amino-2-hydroxycyclopentane may be trans-1-amino-2-indanol. If the trans-1-amino-2-hydroxycyclopentane is trans-(1S,2S)-1-amino-2-indanol, it is converted to cis-(1S,2R)-1-amino-2-indanol; if the trans-1-amino-2-hydroxycyclopentane is trans-(1R,2R)-1-amino-2-indanol it is converted to cis-(1R,2S)-1-amino-2-indanol. When the amino alkanol is partially resolved trans-1-amino-2-indanol, an additional step of recrystallizing the benzamide or acetamide produces substantially optically pure trans-1-amido-2-indanol. The process is particularly useful in the cases of the benzamide or acetamide which readily produce substantially optically pure trans-1-benzamido-2-indanol or trans-1-acetamido-2-indanol respectively.

In a further aspect, the invention relates to a process for producing a cis-1-amino-2-indanol from an indene comprising the steps of:

(a) oxidizing the indene to produce an indene oxide;

(b) converting the indene oxide to an amide of a trans-1-amino-2-indanol; and (c) treating the amide of the trans-1-amino-2-indanol with a solution of a strong acid to cleave the amide and effect inversion of the carbon bearing the hydroxyl function to produce a cis-1-amino-2-indanol.

The trans amide can be made from the epoxide either (1) by treating the indene oxide with ammonia or a primary amine to produce a trans-1-amino-2-indanol and reacting the trans-1-amino-2-indanol with an acylating agent, or (2) by treating the epoxide with an amide anion to produce the trans hydroxy amide directly. In one embodiment the indene is oxidized with aqueous hypochlorite in the presence of a chiral salen catalyst to produce a partially resolved epoxide, which is converted to the partially resolved trans-1-amino-2-indanol by treating with ammonia or a primary amine followed by acylating with benzoyl chloride or acetic anhydride. The resulting benzamide or acetamide is recrystallized to yield substantially optically pure trans-1-benzamido-2-indanol or trans-1-acetamido-2-indanol. In two preferred embodiments, the cis-1-amino-2-indanols are (1S, 2R)-1-amino-2-indanol and (1R,2S)-1-amino-2-indanol, produced by oxidation of indene in the presence of an R,R or S,S-salen catalyst respectively.

In a further aspect the invention relates to a process for producing a compound of formula II

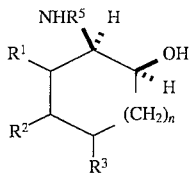

comprising the steps of (a) reacting a trans aminoalcohol of formula III

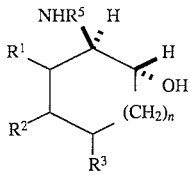

with an acylating agent of formula $R^4CO-X$ to produce an amide of formula IV

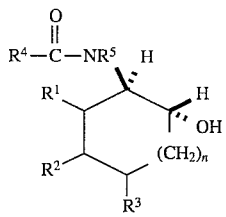

and (b) treating the amide with an aqueous solution of a strong acid, wherein $R^1$ is hydrogen, alkyl, aryl or substituted aryl;
$R^2$ is hydrogen, alkyl, aryl or substituted aryl;
$R^3$ is hydrogen, alkyl, aryl or substituted aryl;
$R^4$ is hydrogen, alkyl, aryl or substituted aryl;
$R^5$ is hydrogen, alkyl, aryl or substituted aryl;
or
$R^1$ and $R^2$ together form a 1,2-fused alicyclic, aryl or substituted aryl residue;
n is zero or an integer from one to three, preferably zero or one; and
X is an activating group for the acylation of amines.

When $R^1$ and $R^2$ together form a 1,2-fused aryl or substituted aryl residue and $R^3$ and $R^5$ are hydrogen, a preferred process may comprise the additional steps of oxidizing an indene to an indene oxide and opening the indene oxide with ammonia to produce the trans-1-amino-2-indanol V.

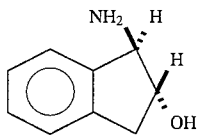

In a further aspect the invention relates to a process for the stereospecific conversion of a trans-1-amino-2-hydroxycyclohexane to the corresponding cis-1-amino-2-hydroxycyclohexane comprising:

(a) reacting a trans-1-amino-2-hydroxycyclohexane with an acylating agent to produce an amide; and (b) treating the amide with an aqueous solution of a strong acid to cleave the amide and effect inversion of the carbon bearing the hydroxyl function to produce a cis-1-amino-2-hydroxycyclohexane.

A preferred trans-1-amino-2-hydroxycyclohexane is trans-1-amino-5,6-benzocyclohexan-2-ol.

In a further aspect the invention relates to a process for the stereospecific conversion of an amide of a trans-1-amino-2-hydroxycyclohexane to the corresponding cis-1-amino-2-hydroxycyclohexane comprising treating the amide with an aqueous solution of a strong acid to cleave the amide and effect inversion of the carbon bearing the hydroxyl function to produce a cis-1-amino-2-hydroxycyclohexane.

In a further aspect the invention relates to amides of trans-1-amino-2-indanols of formula

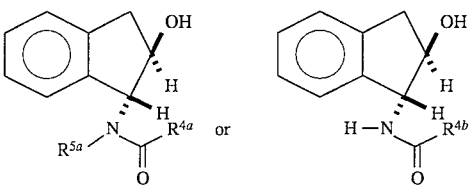

wherein $R^{4a}$ is methyl or phenyl, $R^{4b}$ is alkyl of 1 to 6 carbons, phenyl or substituted phenyl and $R^{5a}$ is hydrogen or alkyl of 1 to 6 carbons and wherein one enantiomer is present in greater than 80% ee. Preferred amides are acetates or benzoates of trans-(1R,2R)-1-amino-2-indanol or of trans-(1S,2S)-1-amino-2-indanol.

In a further aspect the invention relates to trans-1-amino-2-indanols of greater than 80% ee, preferably greater than 90% ee. The invention also relates to substantially optically pure 1-alkylamino-2-indanols wherein alkyl is $C_1$ to $C_6$ hydrocarbon and salts thereof. Among 1-alkylamino-2-indanols, trans-(1S,2S)-1-(methylamino)-2-indanol, trans-(1R,2R)-1-(methylamino)-2-indanol, cis-(1R,2S)-1-(methylamino)-2-indanol, or cis-(1S,2R)-1-(methylamino)-2-indanol are preferred.

DETAILED DESCRIPTION OF THE INVENTION

The central process of the invention comprises reacting an amide of a trans-1-amino-2-cycloalkanol with a strong acid to provide a cis-1-amino-2-cycloalkanol. The result of this process is most unexpected; it would be anticipated that the treatment of an amide with aqueous acid would do no more than hydrolyze the amide, i.e. produce a trans aminoalcohol from a trans amidoalcohol.

The process of the invention can further comprise reaction of a trans-1-amino-2-cycloalkanol with an acylating agent such as an acyl halide or a carboxylic acid anhydride to give the corresponding carboxylic amide, followed by treatment of the amide intermediate under strong acid conditions to give the desired cis-1-amino-2-alkanol in good yield and in only two steps. The present invention is particularly suitable for the preparation of a racemic or optically pure cis-1-amino-2-indanol such as cis-(1S,2R)-1-amino-2-indanol. According to the present invention, an optically pure cis-1-amino-2-indanol can be prepared from an optically pure amide intermediate. The optically pure amide may be obtained by acylation of an optically pure amine or by recrystallization of the amide, particularly the benzamide or acetamide, of partially resolved trans-1-amino-2-indanol.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wedge outlines and dotted or broken lines denote enantiomerically pure compounds of indeterminate absolute configuration; wavy lines indicate disavowal of any stereochemical implication which the bond it represents could generate; and solid and broken bold lines, as in II, III and IV are geometric descriptors indicating the relative configuration shown but denoting racemic character.

The present invention can be more easily understood when reference is made to general Schemes A and B for the preparation of cyclic cis-1-amino-2-alkanols.

Scheme A
(for cyclopentanes)

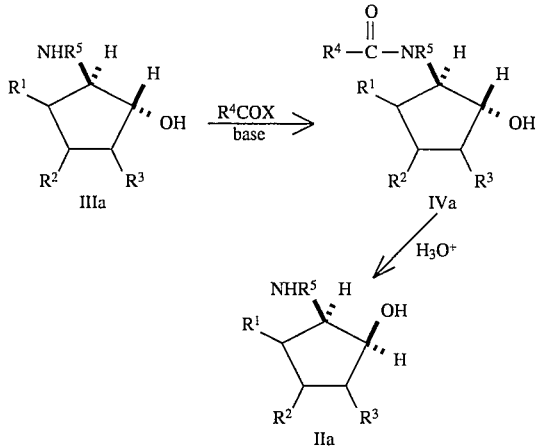

Scheme B
(for cyclohexanes)

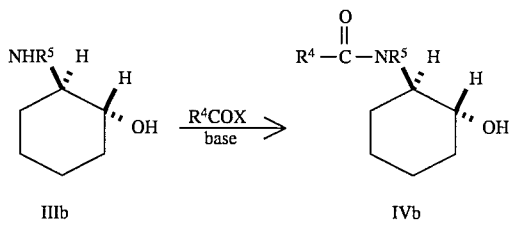

-continued
Scheme B
(for cyclohexanes)

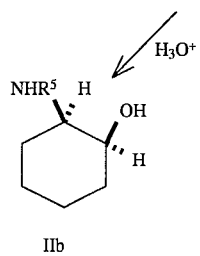

IIb

The trans-1-amino-2-alkanol (III) is reacted with an equal molar or slight excess of an acylating agent to give the amide (II) under basic conditions. The amide is then treated under aqueous conditions in the presence of a strong acid. After basification with bases such as NaOH or KOH, the cis-1-amino-2-alkanol (III) is obtained by simple extraction with an organic solvent such as methylene chloride.

If the starting material (trans aminoalcohol) is racemic, racemic cis aminoalcohol will be produced, as illustrated in Schemes A and B. If the starting material is optically pure trans aminoalcohol, the product will be optically pure (e.g. Scheme A'):

Scheme A'

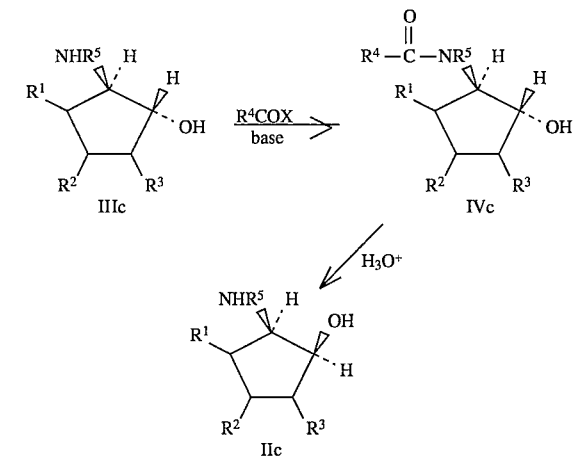

In addition, in the preparation of optically pure cis-1-amino-2-indanol, such as cis-(1S,2R)-1-amino-2-indanol (VI), a partially resolved trans-(1S,2S)-1-amino-2-indanol (IV) can be used. In this case, which is illustrated in Scheme C, the partially resolved trans-1-amino-2-indanol is reacted with benzoyl chloride to give the partially resolved trans-benzamide which is enriched to optically pure trans-benzamide (V) by simple crystallization. The optically pure trans-benzamide is then hydrolyzed under strong acid conditions to give the optically pure cis-(1S,2R)-1-amino-2-indanol (VI).

Scheme C

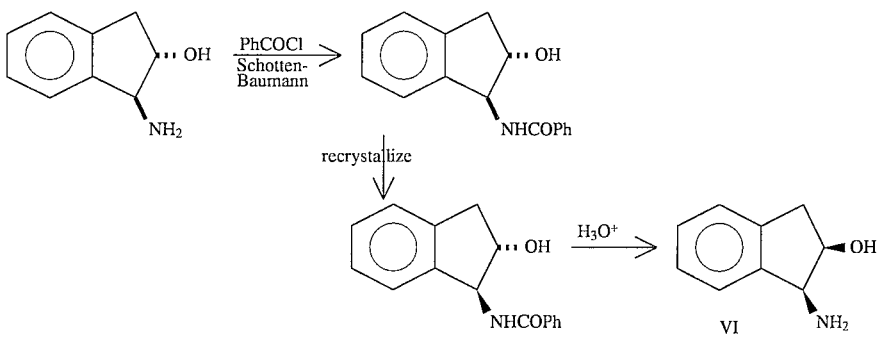

The complete resolution of partially resolved trans benzamide is effective in this case, as it is in the case of other amides of 1-amino-2-indanol, because the enantiomers form a conglomerate or racemic mixture (as opposed to a racemic compound or racemate), and the solubility of the racemic mixture is higher than the solubility of either enantiomer. An enantiomeric excess (ee) of a few percent of either enantiomer in the trans amide will suffice to effect resolution. Mixtures having 80% ee are readily purified to >99% ee in one recrystallization. The term "substantially optically pure" refers to compositions containing >98% ee of a single enantiomer.

As will be understood by persons of skill in the art, the leaving group X in the acylating agent admits of wide variation. Any acylating agent capable of converting an amine to an amide will function in the invention. Thus, the leaving group X can be, for example, a halogen, an activated phenol, an azide, an acyloxy residue (an anhydride) or the like.

The conversion of the trans amide to cis amino-alkanol exhibits high stereoselectivity only when the acid is a strong acid in fairly high concentration. Thus, for example, hydrochloric and sulfuric acids are particularly well suited. Hydrochloric acid should be at least 6 normal; sulfuric acid should be greater than 30%. When concentrations of acid lower than these are used, the hydrolysis still exhibits some stereoselectivity, but the selectivity is not as high as it is in more concentrated solutions. Preferred strong acids are aqueous HCl in the range of 6N–12N or aqueous $H_2SO_4$ in the range of 30–80 wt %, preferably in the range of 50–80 wt %. Methanesulfonic acid, triflic acid (trifluoromethanesulfonic acid), hydrobromic acid and similar strong acids may also be considered; their effective concentration is a matter of simple experimentation which is within the skill of the ordinary artisan. Strong acids are defined as those acids which are completely dissociated in 0.1M aqueous solution.

A temperature in the range of 80°–120° C. is optimal. The reaction should be carried out for sufficient time to allow complete inversion and hydrolysis, usually a period of 3–20 hr.

In order to isolate the basic cis-1-amino-2-alkanol, the reaction mixture is usually basified with a base such as NaOH or KOH to above pH 9, preferably to pH 11–13, and the cis-1-amino-2-alkanol is extracted from the basic aqueous mixture with an inert organic solvent, such as methylene chloride, 1,2-dichloroethane, or a water insoluble alcohol such as n-butanol. After removal of the solvent and further purification using methods standard in organic synthesis, such as distillation and crystallization, the cis-1-amino-2-alkanol is obtained. Alternatively, the cis-1-amino-2-alkanol can be isolated from the reaction by passing the reaction mixture through a basic anion-exchange resin followed by simple isolation.

In the reaction of the trans-1-amino-2-alkanol with an acyl halide or acid anhydride, the acyl halide may be, for example, benzoyl chloride, acetyl chloride, benzoyl bromide, or toluoyl chloride. The acid anhydride may be, for example, benzoic anhydride, acetic anhydride or butyric anhydride. The reaction can be carried out in the presence of an inorganic base such as NaOH or KOH in an inert organic solvent and water mixture such as acetone-water or tetrahydrofuran (THF)-water under standard Schotten-Baumann conditions, or it may be carried out in the presence of an organic base such as triethylamine or 4-dimethylaminopyridine in an inert organic solvent or solvent mixture according to standard organic procedures (J. March *Advanced Organic Chemistry*, 3rd Ed., 370–371 (1985)).

Trans-1-amino-2-alkanols are advantageously prepared by the reaction of ammonia or a primary amine, such as methylamine, with the corresponding epoxide or bromohydrin according to literature methods (R. E. Lutz and R. L. Wayland, Jr. *J. Am. Chem. Soc.* 73, 1639–1641 (1951)). Examples of trans-1-amino-2-alkanols are: racemic trans-1-amino-2-indanol, substituted trans-1-amino-2-indanol and trans-1-amino-5,6-benzocyclohexan-2-ol. Optically pure trans-1-amino-2-indanol can be obtained by the resolution of racemic trans-1-amino-2-indanol with an optically pure chiral acid. In a preferred embodiment of the present invention, partially resolved trans-1-amino-2-indanol is obtained by the reaction of ammonia with partially resolved indene oxide which itself can be made by the asymmetric epoxidation of indene by any of a number of procedures known in the art. A particularly effective procedure utilizes sodium hypochlorite [E. N. Jacobsen et al. *J. Am. Chem. Soc.* 113, 7063–7064 (1991) and references therein]. A preferred catalyst for the chiral oxidation is the salen of formula X

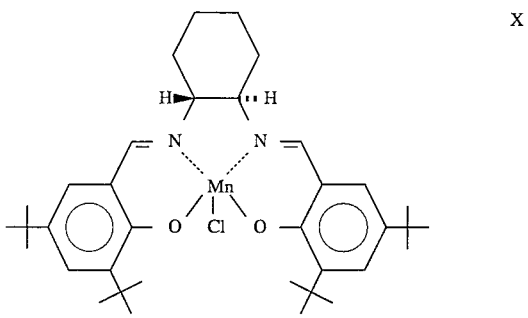

Salens are transition metal complexes of Schiff bases of a salicylaldehyde and a chiral amine. The particular salen shown is of the R,R configuration and provides 80–85% ee of the (1R,2S)-epoxide which can be carried on to the predominantly (S,S)-trans-aminoalcohol. Use of the S,S-salen provides the corresponding (1S,2R)-epoxide in similar fashion. The overall conversion is shown in Scheme D.

Scheme D

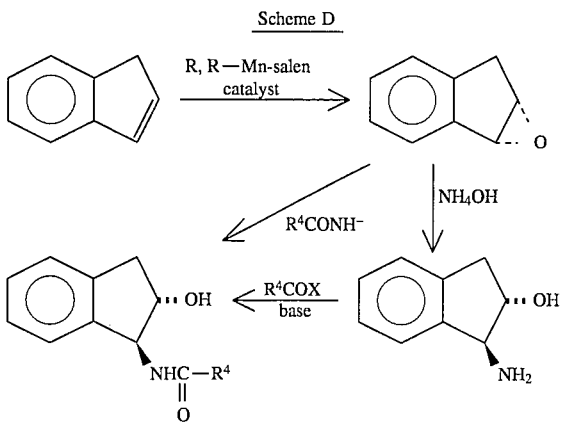

The benzamide, acetamide or similar amide of partially resolved trans-1-amino-2-indanol can be conveniently prepared from the partially resolved indene oxide by reaction of the indene oxide with aqueous ammonia followed by reaction with benzoyl chloride, acetic anhydride, or the appropriate acylating agent in the presence of a base such as NaOH using the Schotten-Baumann procedure without isolation of the trans-1-amino-2-indanol intermediate. Partially resolved trans-benzamide or trans-acetamide of trans-1-amino-2-indanol can be enriched to optically pure trans-benzamide or acetamide by crystallization from an organic solvent such as ethanol (EtOH) or methanol (MeOH) or solvent mixture such as MeOH-dimethylformamide (DMF) or EtOH-DMF. Thus substantially optically pure trans amides, which are synthetically useful, are made available on a commercially attractive scale for the first time. Similarly, the corresponding N-alkylaminoindanols, which are useful as chiral auxiliary agents, are made available by the same sequence of reactions when the indene oxide is opened with an alkylamine in place of ammonia.

An alternative synthesis of the amides of trans-1-amino-2-hydroxycycloalkanes from epoxides, such as indene oxide, can be envisioned wherein the epoxide is opened with an anion, or anion-equivalent, of an amide to create the amide directly from the epoxide. In this case the overall conversion of indene to cis-1-amino-2-indanol can be accomplished in three steps.

In order to fully illustrate the nature of the invention and the manner of practicing the same, the following examples are presented:

EXAMPLE 1

A 5-L three neck Morton-type flask equipped with an overhead stirrer, an addition funnel and a thermometer was charged with 2.5 L of NaOCl (10% aq, 2.0 eq, 4.0 mol). The solution was cooled to ca. 5°–10° C. A solution of (R,R)-Mn-Salen catalyst X (19.1 g, 0.015 eq, 0.03 mol) in 150 mL of $CH_2Cl_2$ was added, followed by a solution of indene (260 mL, 1.0 eq, 2.0 mol) in 100 mL of $CH_2Cl_2$ at 5°–10° C. The mixture was stirred vigorously at 5°–10° C. for 4 hr. Heptane (1.4L) and Celite (40 g) were added and the mixture stirred for 40 min without cooling. The mixture was filtered and the flask and the solid cake were washed with 200 mL of heptane.

The combined filtrates containing partially resolved indene oxide were concentrated to ca. 400 mL and the concentrate treated with 1.4 L of aqueous ammonia (28% aq.) in 600 mL of MeOH in the presence of 20 g of Celite at 25°–30° C. for 15 hr. The MeOH and excess of ammonia were removed by distillation over a period of 4–5 hr until the pot temperature reached 90° C. Water (550 mL) was added and the hot mixture filtered. The flask and solid filter cake were washed with ca. 400 mL of hot water. The combined filtrates were placed under vacuum for 40 min to remove remaining ammonia and transferred to a 5-L Morton-type flask.

The above solution, containing partially resolved trans-(1S,2S)-1-amino-2-indanol, was cooled to ca. 15°–25° C. and NaOH (50% aq., 192 g) and acetone (800 mL) were added. Benzoyl chloride (1.2 eq, 2.4 mol, 280 mL) was added at 15°–25° C. over 1 hr and the resulting slurry stirred at 20°–25° C. for 2 hr. The mixture was filtered and the solid washed with 400 mL of acetone-water (1:1, v/v) and recovered as crude trans-benzamide of partially resolved trans-(1S,2S)-1-amino-2-indanol.

The crude benzamide (ca. 464 g) was dissolved in 1125 mL of DMF at 90° C. and MeOH (750 mL) was added at 80°–86° C. over 1 hour to the DMF solution. The solution was slowly cooled to 0°–5° C. over 1.5 h and held at 0°–5° C. for 2 h. The solid was recovered by filtration, washed with 500 mL cold (0°–5° C.) MeOH and dried under vacuum at 40° C. to give optically pure trans-benzamide of trans-(1S,2S)-1-amino-2-indanol as pale yellow crystals (240 g, 47% yield from indene, 99% ee, m.p. 232° C.).

EXAMPLE 2

A mixture of the trans-benzamide (25 mmol, 6.33 g) from Example 1 and 58.3 mL of 6N aqueous HCl was refluxed for 14 hr, cooled to room temperature, washed with 20 mL of $CH_2Cl_2$ and neutralized with 50% aq. NaOH (24 mL) to about pH 13. The mixture was extracted with total of 65 mL of $CH_2Cl_2$, decolorized with 0.5 g of active carbon, filtered and concentrated to ca. 20 mL. Heptane (10 mL) was added to the hot $CH_2Cl_2$ solution and the solution was cooled to 0°–5° C. for 3 h. The white crystals were recovered by filtration and dried as cis-(1S,2R)-1-amino-2-indanol (2.45 g, 66% yield, 99.5% ee).

EXAMPLE 3

A mixture of the trans-benzamide from Example 1 (25.3 g, 100 mmol) and 196 g of 50% wt of aqueous $H_2SO_4$ was heated at 120–123° C. for 3 h, cooled to room temperature and washed with 100 mL of $CH_2Cl_2$. The aqueous solution was neutralized with 150 mL of 50% aq. NaOH at below 50° C. Water (300 mL) was added to dissolve inorganic salts ($Na_2SO_4$) and the mixture was extracted with a total of 280 mL of $CH_2Cl_2$ at 28°–32° C. The $CH_2Cl_2$ extracts were decolorized with 2 g of active carbon and filtered through Celite. The filtrate was concentrated to ca. 130 mL and 60 mL of heptane was added at 40° C. over 10 min. The solution was cooled to 0°–5° C. over 3 h and the resulting solid recovered by filtration as cis-(1S,2R)-1-amino-2-indanol [10.8 g, 73% yield, $[\alpha]_D^{25}=-65°$ (c=1.0, $CHCl_3$)].

EXAMPLE 4

A mixture of the trans-benzamide from Example 1 (90g, 355 mmol) and 227 g of 80% wt $H_2SO_4$ was heated at 80°–85° C. for 1 h. The mixture was treated with 377 mL of water and heated to 100°–115° C. for 3.5 h. The mixture was cooled to 30°–35° C. and washed with 355 mL of $CH_2Cl_2$. The aqueous solution was then neutralized with 370 g of 50% NaOH at <50° C., and 175 mL water was added to dissolve the inorganic salts ($Na_2SO_4$). The aqueous mixture was extracted with 535 mL of $CH_2Cl_2$ at 30°–35°C., and the $CH_2Cl_2$ extracts decolorized with 4.5 g activated carbon and dried with 7.5 g $MgSO_4$ (anhydrous). The mixture was filtered through Celite and the filter cake washed with 100 mL of $CH_2Cl_2$. The combined filtrates were concentrated to ca. 450 mL and 215 mL heptane was added at 40° C. over 30 min. The solution was cooled to 0°–5° C. and the resulting solid recovered by filtration affording cis-(1S,2R)-1-amino-2-indanol (45.2 g, 84% >99.5% ee).

EXAMPLE 5

A 10 g mixture of the combined filtrates from example 1 containing partially resolved indene oxide were concentrated to about 6 mL and the concentrate (ca 160 mmol) was treated with 124 g of 40% aqueous methylamine in 60mL of methanol. The mixture was stirred at 25°–30° C. for 20 hours. The methanol and excess methylamine were removed by distillation and the mixture was dissolved in 250 mL water, acidified with 7 mL HCl (12M) to pH=1, and washed with 250 mL of methylene chloride. The aqueous solution was neutralized with 15 mL of 50% NaOH at <50° C. to pH>13 and extracted with 250 mL of methylene chloride. The methylene chloride extract was decolorized with 1.5 g activated carbon, dried with 2.5 g of $MgSO_4$ (anhydrous), filtered through Celite and the filter cake was washed with 100 mL of methylene chloride. The combined filtrate was concentrated to about 75 mL and 75 mL heptane was added at 40° C. over 30 min. The solution was cooled to 0°–5° C., and the resulting white solid recovered by filtration. The cake was washed with 50 mL heptane and vacuum dried at 40° C., to afford 4.3 g of trans-(1S,2S)-1-methylamino-2-indanol (35% of theory, 99.4% by HPLC analysis and >99.5%ee, mp=110°–111° C.). Proton and $C^{13}$ NMR were consistent with the proposed structure.

EXAMPLE 6

A solution of 3.0g (18 mmol) of trans-(1S,2S)-1-methylamino-2-indanol of example 5 in 100 mL of water and 40 mL of THF was cooled to 15°–20° C., and 1.76 g (1.2 eq, 21.6 mmol) of 50% NaOH was added dropwise to the stirred solution. Benzoyl chloride (3.1 g, 1.2 eq, 21.6 mmol) was added at 15°–20° C. over 5 min. with stirring. The resulting slurry was cooled to 0°–5° C. and held for 2 hours. The mixture was filtered, and the cake washed with 25 mL water followed by vacuum drying at 40° C., for 5 hours to afford 4.4 g of trans-(1S,2S)-1-benzoylmethylamino-2-indanol (92% of theory, 99.9% HPLC analysis and 99.1%ee, mp=145°–146° C.). Proton and $C^{13}$ NMR were consistent with the proposed structure.

EXAMPLE 7

A mixture of 2.67 g (10 mmol) of the trans-benzamide from Example 6 and 6.4 g of 80% wt $H_2SO_4$ was heated at 80°–85° C. for 1.5 hours. The mixture was then treated with 14.9 g water and heated to 100°–115° C. for 5 hours. The mixture was cooled to 30°–35°, washed with 50 mL of methylene chloride, and the aqueous solution neutralized with 50% NaOH to pH=13. The aqueous mixture extracted with 75 mL of methylene chloride at 30°–35°, the methylene chloride extracts decolorized with 1 g activated carbon and dried with 1.5 g $MgSO_4$ (anhydrous). The mixture was filtered through Celite and the filter cake was washed with 10 mL of methylene chloride. The combined filtrate was concentrated to about 15 mL and 15 mL of heptane was added at 40° C. The slurry was cooled to 0°–5° C. and the resulting white solid was recovered by filtration. Vacuum drying at 40° C. afforded 0.86 g of cis-(1S,2R)-1-methylamino-2-indanol (53% of theory). Proton and $C^{13}$ NMR were consistent with the proposed structure.

EXAMPLE 8

A mixture of 24 g (11 mmol) of racemic trans-2-benzamidocyclohexanol and 12 g of 90% $H_2SO_4$ (110 mmol) was stirred at 75°–80° for 6 hours. After the addition of 22 mL of $H_2O$, the mixture was heated under reflux for 15 hours. The mixture was cooled to room temperature and washed with 20mL of methylene chloride. The acidic aqueous phase was separated, treated with 12.6 mL of 50% NaOH solution (240 mmol) at <40° C., 30mL of $H_2O$ was added and the mixture extracted with a total of 60 mL of methylene chloride at 30°–35° C. The combined extracts were dried over anhydrous $Na_2SO_4$ and filtered. The filtrate was concentrated in vacuo to provide crude product containing cis-2-aminocyclohexanol which was isolated and purified by flash chromatography on silica gel with ethyl acetate-hexane (1:1) to provide 792 mg of cis-2-benzamidocyclohexanol (33% of theory). Proton and $C^{13}$ NMR were consistent with the proposed structure.

EXAMPLE 9

A 3-L three neck Morton flask equipped with an overhead stirrer, 125 mL addition funnel, thermometer, and cooling bath was charged with 1.0 L of NaOCl (10wt % aqueous solution, 2.0 equiv., 1.61 mol). The solution was cooled with vigorous agitation to 5° to 10° C., and 90% indene (106 mL, 0.82 mole) was added at once followed by 20 mL of methylene chloride. A solution of (R,R) salen (X) (7.6 g, 1.5M%) in 80mL of methylene chloride was added to the vigorously stirred mixture over about 5 minutes, and the mixture stirred for about 3 hours until complete by HPLC analysis. Heptane (700 mL) and Celite (15 g) were added and the mixture was stirred for 15 minutes before filtering through a pad of Celite. The filter cake was washed with 100 mL of heptane and the combined filtrates were separated in a separatory funnel. The aqueous waste was treated with sodium sulfite for disposal and the organic phase, containing partially resolved indene oxide, was concentrated to about 150–200 mL under reduced pressure at <50° C.

The concentrate was dissolved in 300 mL of methanol and stirred with 540 mL of aqueous ammonia (28%) and 2.5 g of Celite at 25° to 30° C. for 16 to 24 hours until the reaction was complete by HPLC. The mixture was filtered through Celite under vacuum and the vacuum continued for 30 minutes. (Alternatively, a nitrogen sparge may be introduced for 30 minutes). The filtrate was concentrated until the pot temperature reached 80° to 85° C. During the distillation, 600 mL of water was added. At the end of the distillation, vacuum was applied for 30 minutes to remove residual ammonia.

The filtrate was transferred to a 3-necked, round-bottom flask and tetrahydrofuran (450 mL) and 50% sodium hydroxide (43 mL, 1.2 equiv.) were added with stirring and cooling to 0° to 10° C. The solution was treated with acetic anhydride (78 mL, 1.2 equiv.) over 5 minutes at 0° to 10° C. and stirred until reaction was complete as shown by HPLC (about 2 hours). The resulting slurry was filtered under vacuum, the product cake was washed with 60% v/v aqueous THF (250 mL) and air dried for 30 minutes under vacuum to afford 70.2 g (47% of theory, 85.8%ee) of crude acetamide.

EXAMPLE 10

A mixture of 20 g of the crude acetamide from example 9 and 100 mL of N,N-dimethylformamide was heated at 80° to 85° C. to effect dissolution. The solution was treated dropwise with 75 mL of methanol, cooled slowly to 0° to 5° C. in an ice water bath and held for 1.5 hours. The slurry was collected by vacuum filtration and washed with 50mL of cold methanol to afford, after drying in vacuo at 45° to 50° C., for 16 hours, 13.3 g (66.5% of theory, HPLC, 100%ee) of (1S,2S)-trans-1-acetamido-2-indanol.

EXAMPLE 11

The process stream from the aminolysis analogous to example 9 but employing (S,S)-Salen was treated with 102 mL of HCl (36 wt %) to pH<1.0 and extracted with 500 mL of methylene chloride. The aqueous phase was basified with 50% sodium hydroxide to pH=13 and extracted with 600 mL of methylene chloride at 30° to 35° C. The methylene chloride extracts were decolorized with 6.0 g of Darco G-60® and dried with 7.5 g of magnesium sulfate (anhydrous) at 30° to 35° C. The mixture was vacuum filtered and washed with 150 mL of methylene chloride. The filtrate was heated to reflux and 750 mL of heptane was added dropwise at 40° to 45° C. The slurry was cooled to 0° to 5° C. and held for three hours. The off-white product was collected by vacuum filtration and washed with 50 mL of heptane followed by drying in vacuo at 40° C., for 5 hours to afford 97.9 g (65.6% of theory, 94.7%ee) of (R,R)-trans-1-amino-2-indanol.

EXAMPLE 12

A solution of 5g (33.5 mmol) of (R,R)-trans-1-amino-2-indanol of example 11 in tetrahydrofuran (40 mL) and water (60 mL) was treated with 50% sodium hydroxide (2.1 mL, 1.2 equiv.) with stirring and cooling to 0° to 10° C. The resulting solution was treated with acetic anhydride (3.8 mL, 1.2 equiv.) over 5 minutes at 0° to 10° C. The mixture was stirred until reaction appeared complete by HPLC (about 2 hours) and the resulting slurry was filtered under vacuum. The product cake was washed with water (25 mL) and air dried under vacuum for 72 hours to afford 4.2 g (66% of theory, 100%ee) of (1R,2R)-trans-1-acetamido-2-indanol.

We claim:

1. A substantially optically pure 1-alkylamino-2-indanol or salt thereof wherein alkyl is $C_1$ to $C_6$ hydrocarbon.

2. A compound according to claim 1 chosen from the group consisting of trans-(1S,2S)-1-(methylamino)-2-indanol, trans-(1R,2R)-1-(methylamino)-2-indanol, cis-(1R,2S)-1-(methylamino)-2-indanol, or cis-(1S,2R)-1-(methylamino)-2-indanol.

3. An enantiomer of trans-1-amino-2-indanol of greater than 80% ee, or salt thereof.

4. (1R,2R)-1-Amino-2-indanol of greater than 90% ee, or salt thereof according to claim 3.

5. (1S,2S)-1-Amino-2-indanol of greater than 90% ee, or salt thereof according to claim 3.

* * * * *